United States Patent
Rajic et al.

[11] Patent Number: 5,923,421
[45] Date of Patent: Jul. 13, 1999

[54] CHEMICAL DETECTION USING CALORIMETRIC SPECTROSCOPY

[75] Inventors: Slobodan Rajic; Panagiotis G. Datskos, both of Knoxville, Tenn.

[73] Assignee: Lockheed Martin Energy Research Corporation, Oak Ridge, Tenn.

[21] Appl. No.: 08/899,978

[22] Filed: Jul. 24, 1997

[51] Int. Cl.[6] .............................. G01J 3/28; G01N 21/29
[52] U.S. Cl. ...................................... 356/328; 422/82.05
[58] Field of Search .............................. 422/82.02, 82.05, 422/82.09, 55; 356/328

[56] References Cited

U.S. PATENT DOCUMENTS

| | | | |
|---|---|---|---|
| 3,999,122 | 12/1976 | Winstel et al. | 324/71 |
| 4,146,887 | 3/1979 | Magnante | 340/632 |
| 4,827,246 | 5/1989 | Dolan et al. | 340/521 |
| 5,124,172 | 6/1992 | Burrell et al. | 427/2 |
| 5,140,120 | 8/1992 | Kasai et al. | 219/10.55 |
| 5,179,002 | 1/1993 | Fehder | 435/25 |
| 5,268,145 | 12/1993 | Namba et al. | 422/57 |
| 5,447,614 | 9/1995 | Hamamure et al. | 204/192.33 |
| 5,464,588 | 11/1995 | Bather et al. | 422/88 |
| 5,591,321 | 1/1997 | Pyke | 205/787 |
| 5,621,522 | 4/1997 | Ewing et al. | 356/301 |
| 5,663,050 | 9/1997 | Bedell | 435/7.23 |

*Primary Examiner*—Frank G. Font
*Assistant Examiner*—Zandra V. Smith
*Attorney, Agent, or Firm*—Quarles and Brady

[57] ABSTRACT

A chemical detector comprises: an array of sensing elements, each having a characteristic physical parameter and a coating exhibiting a preferential adsorption of a chemical to be sensed; a chamber for exposing the coatings to an unknown sample of a chemical to be analyzed, the coatings adsorbing the chemical if present in the sample; a source of a monochromatic spectrum for radiating the array with different monochromatic wavelengths; and, a controller for recording signals representative of the physical parameter of the sensing elements responsive to the radiation. A method for sensing chemicals comprises the steps of: preferentially adsorbing a chemical to be sensed onto an array of sensing elements having a characteristic physical parameter; exposing the coatings to an unknown sample of a chemical to be analyzed, the coatings adsorbing the chemical if present in the sample; radiating the sensing elements with different monochromatic wavelengths; and, measuring changes of the physical parameter due to the adsorbing. The measurable changes of the physical parameter due to the adsorbing define a unique photothermal signature of a detected chemical. The arrays can be linear or multi dimensional, for example two dimensional.

37 Claims, 4 Drawing Sheets

CHEMICAL DETECTION USING CALORIMETRIC SPECTROSCOPY

BACKGROUND OF THE INVENTION

1. Field of the Invention

This invention relates to the field of calorimetric spectroscopy, and in particular, to thermal detectors having miniature chemical sensors for detecting minute amounts of chemical analytes.

2. Description of Related Art

Determining the presence and identity of unknown chemical species is challenging. Presently available chemical sensors that can detect the presence and identity of unknown chemical analytes with enhanced sensitivity are either too large, too cumbersome, lack high selectivity and specificity or too costly for most purposes.

Chemical analysis has been undertaken in a number of different ways, including spectral analysis and thermal analysis. An apparatus used in spectral analysis is the monochromator. A monochromator is a device for isolating a narrow portion of a spectrum. Apparatus which can be used as thermal detectors in thermal analysis include, for example, bolometers, thermopiles, pyroelectrics and micro cantilevers. A bolometer, for example, is a very sensitive thermometer whose electrical resistance varies with temperature and which is used in the detection and measurement of feeble thermal radiation. Bolometers have been especially useful in the study of infrared spectra.

SUMMARY OF THE INVENTION

In accordance with the inventive arrangements taught herein, a chemical sensor capable of the selective and sensitive detection of chemical analytes comprises a monochromator and a thermal infrared detector array, for example, a micro bolometer, a thermopile, a pyroelectrics or a micro cantilever. Such a chemical sensor can detect the presence of minute amounts of chemical analytes, for example less than parts per trillion (ppt), with increased selectivity by allowing a simultaneous determination of the identity of the unknown species.

A thermal detector surface is provided with an active detector surface of individual sensing elements coated with an appropriate chemical layer having an affinity for a family or a group of the target chemical or chemicals and placed into a chamber into which a sample is drawn. The use of highly selective chemical coatings is not required As the sampling continues, molecules of the target chemicals adsorb on the thermal detector surface causing a measurable change in the thermal detector. If a micro bolometer is used as the thermal detector, for example, its electrical resistance will change during the adsorption. After this passive sampling is complete, a photothermal spectrum can be obtained for the chemicals adsorbed on the thermal detector surface by scanning a broad band wavelength region with the aid of a monochromator or other tunable sources including, for example, light emitting diodes and tunable lasers. During this active sampling, the temperature of the particular detector pixels for the wavelengths at which the adsorbed chemical absorbs photons will rise proportionally to the amount of analyte deposited and heat absorbed. Signal-to-noise ratios and detection speed are both improved. Since different pixels will be exposed to different wavelengths, a very sensitive and unique photothermal signature response can thus be obtained. Since the passive sampling is not selective and can be measured only in real time, the passive sampling can act as a trigger for the active sampling.

Advantageously, the thermal detector surface can be easily regenerated after the test, for example by ohmic heating of the detector element or by focusing the radiation from a hot blackbody radiation source or laser source onto the detector surface.

A chemical detector in accordance with an inventive arrangement comprises: an array of sensing elements, each of the sensing elements having a characteristic physical parameter and each of the sensing elements having a coating exhibiting a preferential adsorption of at least one chemical to be sensed; means for exposing the coatings to an unknown sample of at least one chemical to be analyzed, the coatings adsorbing the at least one chemical to be sensed if present in the sample; a source of a monochromatic spectrum for respectively radiating the array of sensing elements with different wavelengths of the monochromatic spectrum; and, means for recording signals representative of the physical parameter of each of the sensing elements in the array responsive to the radiation of the different wavelengths, measurable changes of the physical parameter due to the adsorbing defining a unique photothermal signature of a detected chemical.

The array can comprise a one dimensional array having one row of the sensing elements or a multi dimensional array, for example a two dimensional array, having respective rows of the sensing elements. The sensing elements of the respective rows can have different coatings for preferentially adsorbing different chemicals.

The array of sensing elements advantageously comprises a thermal detector. The detector array of sensing elements can, for example, comprise: a bolometer array; a thermopile array; a pyroelectric array; or a micro cantilever array.

The exposing means can comprise a chamber in which the array can be disposed and into which the sample can be admitted.

In the presently preferred embodiment, the detector can comprise a housing having an infrared transmissive panel defining a first chamber in which the array is disposed and into which the sample can be admitted and a second chamber in which the monochromator is disposed, the monochromator being thereby isolated from the sample. The first chamber can have a membrane for admitting the sample into the first chamber and an aperture for coupling the first chamber to a differential pump for drawing the sample through the membrane and into the first chamber.

The detector can further comprise means for heating the sensing elements to effect desorption of sensed chemicals.

A method for sensing chemicals in accordance with another inventive arrangement comprises the steps of: preferentially adsorbing at least one chemical to be sensed onto an array of sensing elements having a characteristic physical parameter; exposing the coatings to an unknown sample of at least one chemical to be analyzed, the coatings adsorbing the at least one chemical to be sensed if present in the sample; respectively radiating the sensing elements with different wavelengths of a monochromatic spectrum; and, measuring changes of the physical parameter due to the adsorbing, the measured changes defining a unique photothermal signature of a detected chemical.

The method can comprise the step of recording signals representative of the measured changes.

In a presently preferred embodiment, the method comprises the step of preferentially adsorbing the at least one chemical to be sensed onto an array of sensing elements, for example thermal sensing elements.

In the presently preferred embodiment, the method comprises one or more of the following steps: generating the monochromatic spectrum of radiation with a broad band light source and a monochromator; first applying to the sensing elements a coating exhibiting a preferential adsorption of at the least one chemical to be sensed; exposing the coatings to the unknown sample in a chamber in which the array is disposed and admitting the sample into the chamber; and, radiating the different wavelengths of the monochromatic spectrum into the chamber through an infrared transmissive panel.

The method can further comprise the step of desorbing the sensed chemicals, for example, by briefly heating the thermal detectors to a temperature high enough to desorb the sensed chemicals without damaging the thermal detectors or coatings.

A spectrometer in accordance with yet another inventive arrangement comprises: a plurality of sensing elements in an array, each of the sensing elements having a coating exhibiting a preferential adsorption of at least one chemical to be sensed; means for exposing the coatings to an unknown sample of at least one chemical to be adsorbed by the coatings as an analyte if present in the sample; a source of a monochromatic spectrum for preferentially illuminating the thermal detectors according to quantities of the adsorbed analyte; and, means for recording signals representative of respective thermal conditions of each of the sensing elements in the array responsive to the monochromatic illumination, the recorded signals exhibiting improved signal-to-noise ratios.

The array, which can be a linear array or a multi dimensional array, can be illuminated in a transmission mode or in a reflection mode.

BRIEF DESCRIPTION OF THE DRAWINGS

There are shown in the drawings forms which are presently preferred, it being understood, however, the inventive arrangements are not limited to the precise arrangements and instrumentalities shown.

DETAILED DESCRIPTION OF THE PREFERRED EMBODIMENTS

Figure 1:
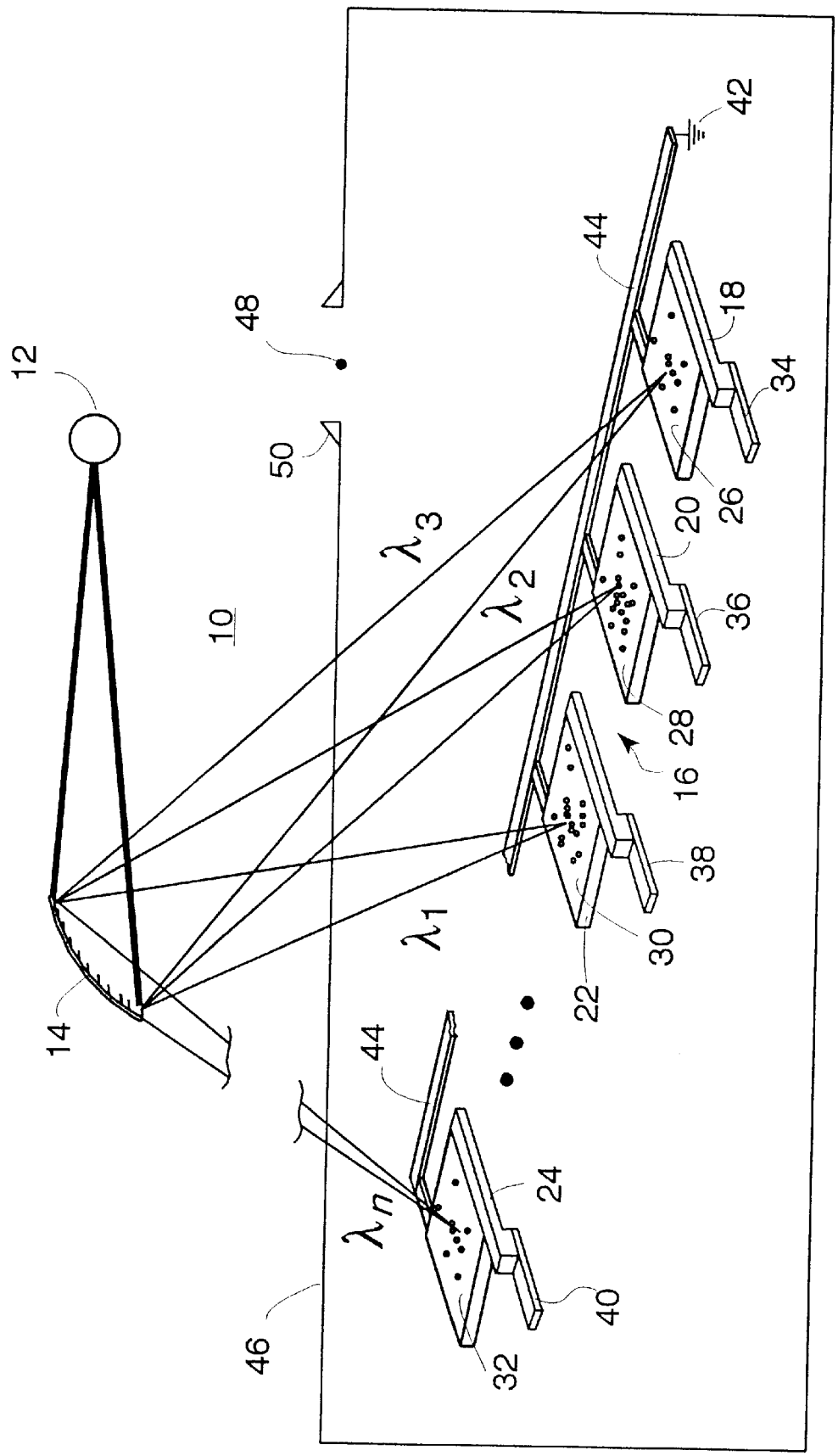
FIG. 1 is a diagrammatic representation of a chemical detector in accordance with an inventive arrangement.

A chemical detector in accordance with the inventive arrangements taught herein, and capable of the selective and sensitive detection of chemical analytes, is shown in FIG. 1. The chemical detector, generally designated by reference numeral 10, comprises a broad band light source 12, a monochromator 14 and an array 16 of sensing elements, for example thermal sensing elements. The array forms a thermal infrared detector array and in a presently preferred embodiment is advantageously embodied as a micro bolometer, as shown. Chemical detector 10 can detect the presence of minute amounts of chemical analytes, for example less than parts per trillion (ppt), with increased selectivity by allowing a simultaneous determination of the identity of the unknown species.

The thermal detector array 16 comprises a plurality of individual sensing elements 18, 20, 22, . . . , 24. The individual sensing elements are provided with respective active detector surfaces 26, 28, 30, . . . , 32 coated with an appropriate chemical layer having an affinity for the family or group of the target chemical or chemicals. A layer of gold, for a first example, can be utilized for detecting mercury or sulfur containing chemicals. A layer of hydrated silica or platinum or other gas chromatograph coating, for a second example, can be utilized for detecting trinitrotoluene (TNT). The use of highly selective chemical coatings is not required. The application of the chemical layer corresponds to a first step of a method in accordance with the inventive arrangements.

The sensing elements have respective read out terminals 34, 36, 38, . . . , 40, but are coupled to a source of ground potential 42 by a common bus 44. The sensing elements have a characteristic physical parameter which can be measured. In the case of a bolometer, for example, this parameter is electrical resistance. In the case of a micro cantilever, for example, this parameter is the amount of bending. The read out terminals provide respective electrical signals representative of the physical parameter of the individual sensing elements.

The array 16 is placed into a chamber 46, into which a sample is drawn through an inlet or opening 48 defined by a valve 50, shown diagrammatically by a conical ring.

As passive sampling continues, molecules of the target chemicals adsorb on the coated individual sensing elements. This adsorption will result in physical changes on the thermal detectors. If a micro bolometer is used as the thermal detector, for example, its electrical resistance will change during the adsorption. If a micro cantilever is used as the thermal detector, for example, its bending characteristics will change during the adsorption. If a thermopile array is used as the thermal detector, for example, its voltage will change during the adsorption. If a pyroelectric array is used as the thermal detector, for example, its capacitance and/or current will change during the adsorption. Exposing the sensing elements to the sample, in a chamber as described, or otherwise, is a further method step.

After adsorption and passive sampling are complete, a photothermal spectrum can be obtained for the chemicals adsorbed on the surfaces of the sensing elements by scanning a broad band wavelength region with the aid of the broad band light source 12 and the monochromator 14. In this active sampling scheme, the monochromator 14 directs different wavelengths of light onto different ones of the individual sensing elements in the array 16. The array 16 can be removed from the chamber 46 or the chamber 46 can be provided with another aperture or opening, or infrared transmissive window or panel, for the light coming from the monochromator 14. Removing the array 16 from contact with or exposure to the sample, by evacuating the sample from chamber 46 and/or removing the array 16 from the chamber 46, or otherwise terminating the exposure, is another method step.

In FIG. 1, light of wavelength $\lambda_1$ is directed from the monochromator 14 to detector 22, light of wavelength $\lambda_2$ is directed from the monochromator 14 to detector 20 and light of wavelength $\lambda_3$ is directed from the monochromator 14 to detector 18. For the different ones of the wavelengths $\lambda_1$, $\lambda_2$ and $\lambda_3$, . . . , $\lambda_n$ at which the adsorbed chemical or chemicals absorb photons, the temperature of those particular detector pixels will rise proportionally to the amount of analyte deposited at specific wavelengths on the detector surface, and in turn, the amount of heat absorbed by the deposited analyte. Since pixels on different ones of the individual detectors will be exposed to different ones of the wavelengths by the action of the monochromator 14, a very sensitive and unique photothermal signature response, or spectrum, across the array 16 can thus be obtained. In the presently preferred embodiment utilizing the micro bolometer, this spectrum is based on the respective resistance changes of the individual sensing elements. In an alternative embodiment utilizing micro cantilevers, for example, this spectrum is based on the respective bending characteristics of the individual sensing elements. The detection resolution depends on the quality of the optical system and the density and number of thermal detector array pixels used in the array. Recording and processing the photothermal signature, indicative of the spectral response of the detector array 16, are yet further method steps.

Figure 2:
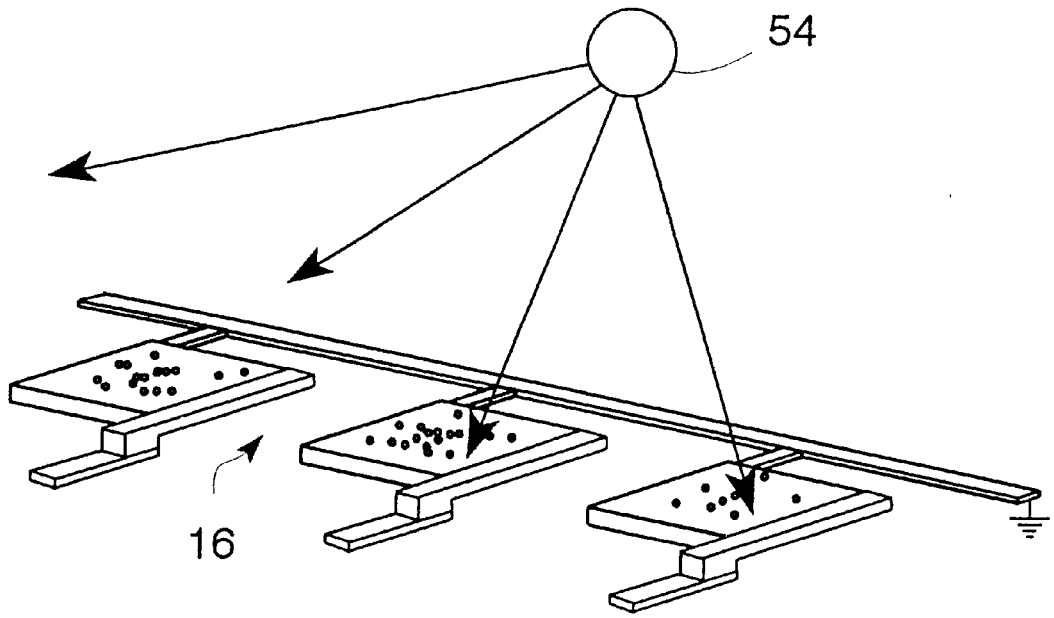
FIG. 2 is a diagrammatic representation of a first alternative for regenerating the surface of the thermal detector array shown in FIG. 1.
Figure 3:
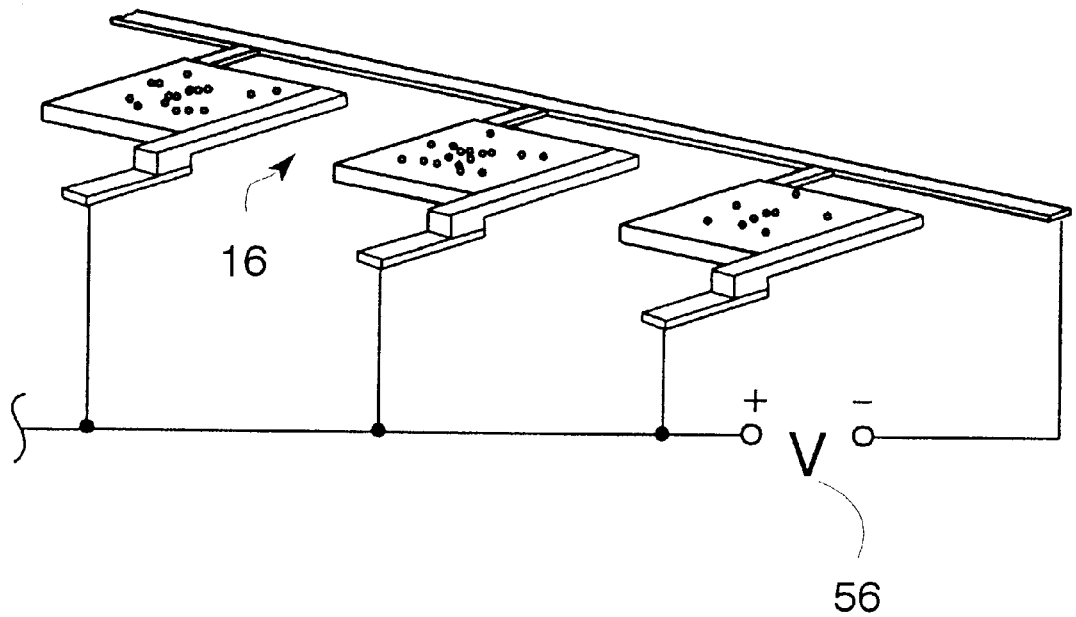
FIG. 3 is a diagrammatic representation of a second alternative for regenerating the surface of the thermal detector array shown in FIG. 1.

After the test, the thermal detector surface, formed by the sensing elements, can be regenerated by heating the array 16. One alternative, for example, is by focusing the radiation from a hot blackbody radiation source or a laser source onto the detector, such a source being generally designated by reference numeral 54 in FIG. 2. Another alternative, for example, is by ohmic heating of the detector element, as shown in FIG. 3, utilizing a source 56 of high voltage potential V. Since the mass of a pixel element can be very small, for example approximately $10^{-9}$ gm, its temperature can rise significantly, for example in excess of 500° C., within a very short time and responsive to low power, thus causing a desorption of the analytes from the surface of the sensing element without damage to the surface of the thermal detector. Regenerating the array can be a final method step.

Figure 4:
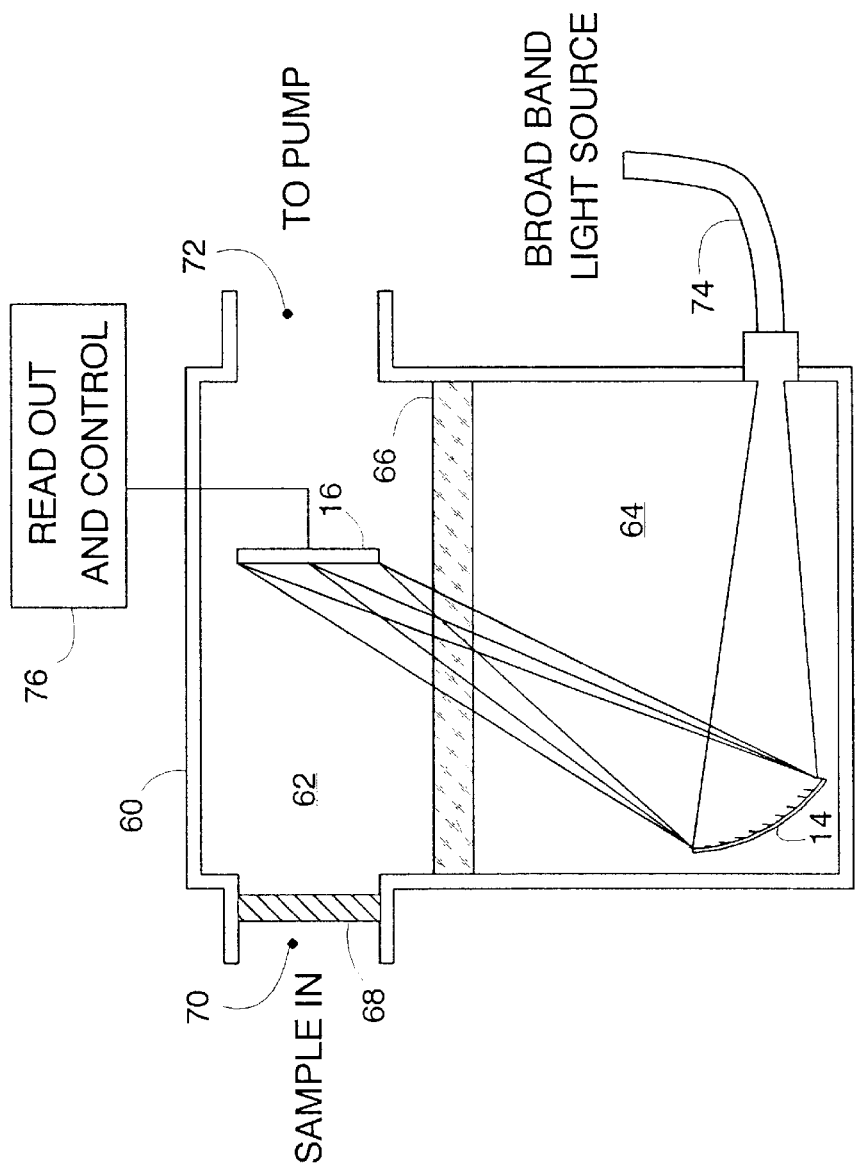
FIG. 4 is a complete diagrammatic representation of a presently preferred embodiment.

A more specific representation of a presently preferred embodiment of a chemical sensor is shown diagrammatically in FIG. 4 and generally designated by reference numeral 58. The sensor 58 comprises a housing 60 having a first chamber 62 and a second chamber 64, formed by an infrared transmissive window 66. Suitable materials for the window 66 are, for example, ZnSe, ZnS or other infrared transmissive materials which can be maintained at a higher temperature compared to the rest of the detector in order to minimize unwanted adsorption. The detector, for example a thermal detector, is formed by an array 16 of sensing elements disposed in the chamber 62. The sensing elements can be, for example, bolometers, thermopiles, pyroelectrics or micro cantilevers. The monochromator 14 is disposed in the chamber 64. The output of a broad band light source is delivered into the chamber 64 by an optical fiber 74, the broad band light being directed onto the monochromator 14.

The sample having the chemical or chemicals to be sensed is drawn into the chamber 62 through a membrane 68 in an opening or aperture 70 by the action of a vacuum pump, connected to an opening or aperture 72. Suitable materials for the membrane should be able to block unwanted chemical interferences, as appropriate, from entering the sampling chamber. One suitable material for the membrane, for example, is dimethyl silicone, which can block water vapor. The sample is thereby drawn into intimate contact with the surface coatings on the array 16, but isolated from contact with the monochromator 14.

The photothermal signatures are recorded and processed by the read out and control circuitry 76.

The embodiment shown in FIG. 4 is advantageous for a number of reasons. Firstly, the monochromator is protected from any damage or degradation which might result from contact with the sample. Secondly, it is unnecessary to remove either the monochromator or the array from their respective chambers in the housing during any part of the chemical sensing or regeneration of the coating surfaces. As a consequence, the optical paths between the broad band light source and the monochromator in the chamber 64, and between the monochromator and the array, do not need frequent alignment. Thirdly, neither the array nor the monochromator will be subjected to light from any unintended sources, although the broad band light source can be easily changed without effecting the optical paths. Fourthly, the broad band light source can be placed in almost any position relative to the monochromator, the array and the housing.

In accordance with yet another inventive arrangement, a thermal detector and a monochromator are employed to significantly improve the signal-to-noise ratio for more traditional spectroscopy. As in the apparatus and method described above, small amounts of analyte would be adsorbed or reacted with the chemical coating on the detector array 16. The array 16 can then serve as a linear thermal detector for a conventional spectrometer. Since the monochromator 14 will preferentially illuminate the different detector pixels according to the chemistry present in either of the transmission or reflection modes, a substantial increase in signal-to-noise ratio will be observed for those pixels relative to the others. This is particularly important for marginally resolvable situations, where the signal-to-noise ratio is less than 3, or even less than 2.

The inventive arrangements taught herein provide many advantages over known chemical sensors. The inventive arrangements provide selective and sensitive detection of chemical analytes with great inherent simplicity and reliability, without the need for highly selective chemical coatings, at low cost, in a form which is relatively easy to build and in a form which is particularly amenable to miniaturization.

Figure 5:
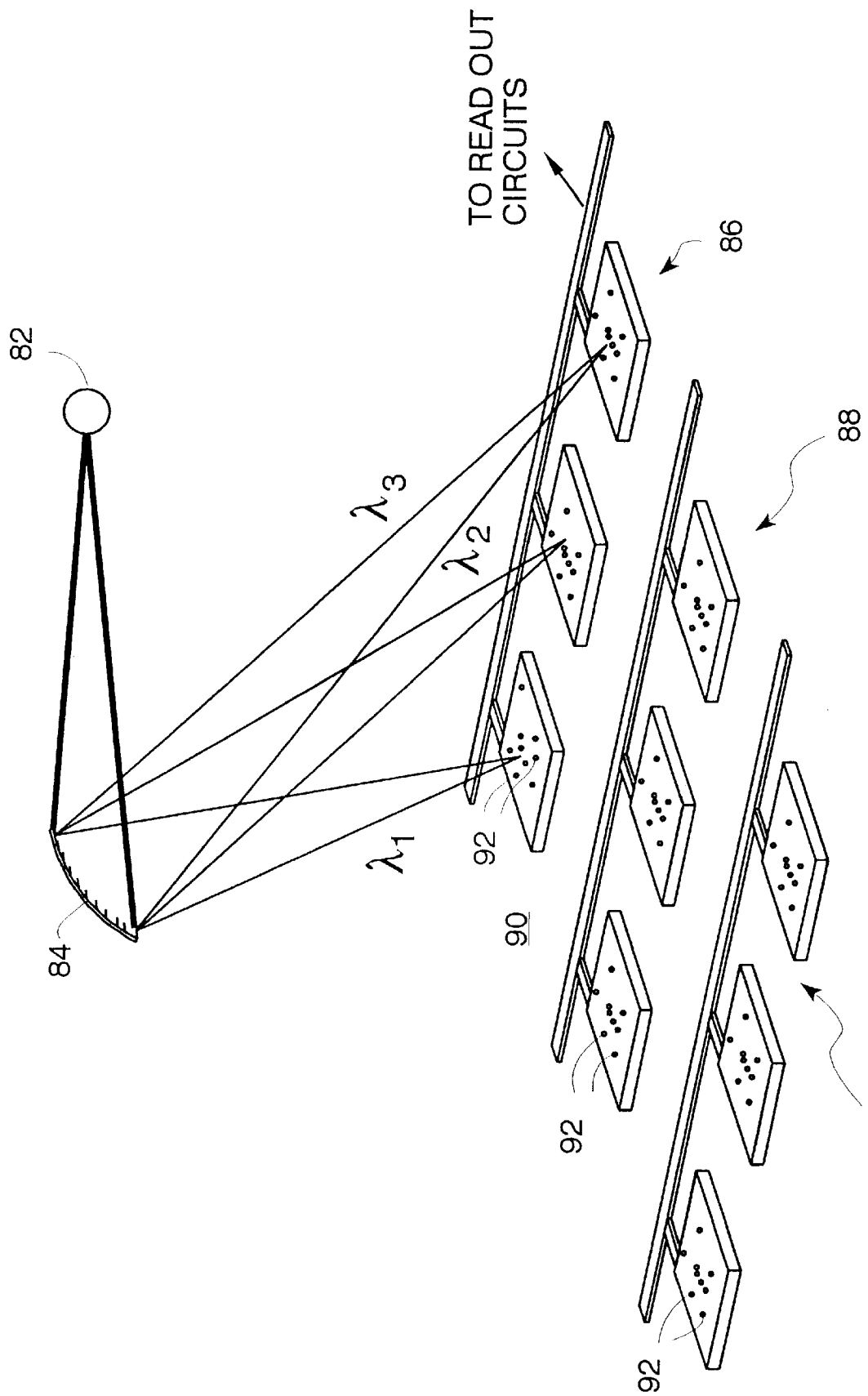
FIG. 5 is a diagrammatic representation of a two dimensional chemical detector.

The thermal detector arrays need not be limited to one dimensional arrays. Multi dimensional arrays can also be utilized. A two dimensional thermal detector array 80, for example, is shown in FIG. 5. The two dimensional array 80 operates in conjunction with a broad band light source 82 and a monochromator 84, of the kinds already described in connection with FIGS. 1–4. The two dimensional array 80 comprises a plurality of rows of sensing elements, in this case, three rows designated by reference numerals 86, 88 and 90. Each row can advantageously be coated with a different chemical coating than the other rows for targeting more than one chemical or family of chemicals in the same test sampling. Adsorbed target molecules are also illustrated, designated by reference numeral 92.

The invention may be embodied in other specific forms without departing from the spirit or essential attributes thereof. Reference should be made to the appended claims, rather than to the foregoing specification, as indicating the true scope of the inventive arrangements.

What is claimed is:

1. A chemical detector, comprising:
   an array of sensing elements, each of said sensing elements having a measurable characteristic physical parameter and each of said sensing elements having a coating exhibiting a preferential adsorption of at least one chemical to be sensed;
   means for exposing said coatings to an unknown sample of at least one chemical to be analyzed, said coatings adsorbing said at least one chemical to be sensed if present in said sample;

a source of a monochromatic spectrum for respectively radiating and thereby heating said array of sensing elements with different wavelengths of said monochromatic spectrum, said physical parameter of said sensing elements being changed by said adsorbing; and, means for recording signals representative of said physical parameter of each of said sensing elements in said array responsive to said radiation of said different wavelengths, measurable changes of said characteristic physical parameter of said sensing elements due to adsorbing said chemical defining a unique photothermal signature of a detected chemical.

2. The detector of claim 1, wherein said array is a one dimensional array having one row of said sensing elements.

3. The detector of claim 1, wherein said array is a two dimensional array having respective rows of said sensing elements.

4. The detector of claim 3, wherein said sensing elements of said respective rows have different coatings for preferentially adsorbing different chemicals.

5. The detector of claim 3, wherein said physical parameter is electrical resistance.

6. The detector of claim 1, wherein said array is a multi dimensional array having respective rows of said sensing elements.

7. The detector of claim 6, wherein said sensing elements of said respective rows have different coatings for preferentially adsorbing different chemicals.

8. The detector of claim 1, wherein said array of sensing elements comprises a thermal detector.

9. The detector of claim 1 wherein said array of sensing elements comprises a balometer array.

10. The detector of claim 1 wherein said array of sensing elements comprises a thermopile array.

11. The detector of claim 10, wherein said physical parameter is voltage.

12. The detector of claim 10, wherein said physical parameter is current.

13. The detector of claim 1, wherein said array of sensing elements comprises a pyroelectric array.

14. The detector of claim 13, wherein said physical parameter is capacitance.

15. The sensor of claim 1, wherein said exposing means comprises a chamber in which said array is disposed and into which said sample can be admitted.

16. The sensor of claim 1, wherein said source of said monochromatic spectrum of radiation comprises:
    a broad band light source; and,
    a monochromator.

17. The sensor of claim 1, further comprising means for heating said sensing elements to effect desorption of sensed chemicals.

18. A chemical detector, comprising:
    an array of sensing elements micro cantilever sensing elements, each of said sensing elements having a characteristic physical parameter and each of said sensing elements having a coating exhibiting a preferential adsorption of at least one chemical to be sensed;
    means for exposing said coatings to an unknown sample of at least one chemical to be analyzed, said coatings adsorbing said at least one chemical to be sensed if present in said sample;
    a source of a monochromatic spectrum for respectively radiating said array of sensing elements with different wavelengths of said monochromatic spectrum; and,
    means for recording signals representative of said physical parameter of each of said sensing elements in said array responsive to said radiation of said different wavelengths, measurable changes of said physical parameter due to said adsorbing defining a unique photothermal signature of a detected chemical.

19. The detector of claim 18, wherein said physical characteristic is bending of said micro cantilevers.

20. A chemical detector, comprising:
    an array of sensing elements, each of said sensing elements having a characteristic physical parameter and each of said sensing elements having a coating exhibiting a preferential adsorption of at least one chemical to be sensed;
    means for exposing said coatings to an unknown sample of at least one chemical to be analyzed, said coatings adsorbing said at least one chemical to be sensed if present in said sample;
    a source of a monochromatic spectrum for respectively radiating said array of sensing elements with different wavelengths of said monochromatic spectrum;
    a housing having an infrared transmissive panel, with a minimized adsorption characteristic, defining a first chamber in which said array is disposed and into which said sample can be admitted and a second chamber in which said monochromator is disposed, said monochromator being thereby isolated from said sample; and,
    means for recording signals representative of said physical parameter of each of said sensing elements in said array responsive to said radiation of said different wavelengths, measurable changes of said physical parameter due to said adsorbing defining a unique photothermal signature of a detected chemical.

21. The sensor of claim 20, wherein said first chamber has a membrane for admitting said sample into said first chamber and an aperture for coupling said first chamber to a pump for drawing said sample through said membrane and into said first chamber.

22. A method for sensing chemicals, comprising the steps of:
    preferentially adsorbing at least one chemical to be sensed onto an array of sensing elements having a measurable characteristic physical parameter;
    measurably changing said characteristic physical parameter of said sensing elements by exposing said coatings to an unknown sample of at least one chemical to be analyzed, said coatings adsorbing said at least one chemical to be sensed if present in said sample;
    respectively heating said sensing elements by radiating said sensing elements with different wavelengths of a monochromatic spectrum;
    measuring said changing of said physical parameter of said sensing elements due to said adsorbing; and,
    defining a unique photothermal signature of a detected chemical with said measurable changes of said physical parameter.

23. The method of claim 22, comprising the step of recording signals representative of said measured changes.

24. The method of claim 22, comprising the step of first applying to said sensing elements a coating exhibiting a preferential adsorption of at said least one chemical to be sensed.

25. The method of claim 22, comprising the steps of:
    exposing said coatings to said unknown sample in a chamber in which said array is disposed; and,
    admitting said sample into said chamber.

26. The method of claim 22, comprising the step of generating said monochromatic spectrum of radiation with a monochromator.

27. The method of claim 22, wherein said radiating step comprises the step of radiating a broad band light source onto a monochromator.

28. The method of claim 22, further comprising the step of desorbing said sensed chemicals.

29. The method of claim 22, further comprising the step of briefly heating said sensing elements to a temperature high enough to desorb said sensed chemicals without damaging said sensing elements.

30. The method of claim 22, comprising the step of preferentially adsorbing a plurality of chemicals to be sensed onto a multi dimensional array having respective rows of said sensing elements, said sensing elements of said respective rows having different coatings for preferentially adsorbing different chemicals.

31. The method of claim 25, comprising the step of radiating said different wavelengths of said monochromatic spectrum into said chamber through an infrared transmissive panel.

32. A spectrometer, comprising:

a plurality of sensing elements in an array, each of said sensing elements having a coating exhibiting a preferential adsorption of at least one chemical to be sensed and each of said sensing elements having a measurable physical characteristic;

means for exposing said coatings to an unknown sample of at least one chemical to be adsorbed by said coatings as an analyte if present in said sample, said physical parameter of said sensing elements being changed by said adsorbing;

a source of a monochromatic spectrum for preferentially illuminating and heating said thermal detectors according to quantities of said adsorbed analyte; and, means for recording signals representative of said measurable changes of said physical parameter of each of said sensing elements in said array responsive to said heating by said monochromatic illumination, said recorded signals exhibiting improved signal-to-noise ratios.

33. The spectrometer of claim 32, wherein said array is illuminated in a transmission mode.

34. The spectrometer of claim 32, wherein said array is illuminated in a reflection mode.

35. The detector of claim 32, wherein said array is a one dimensional array having one row of said sensing elements.

36. The detector of claim 32, wherein said array is a two dimensional array having respective rows of said sensing elements.

37. The detector of claim 36, wherein said sensing elements of said respective rows have different coatings for preferentially adsorbing different chemicals.

* * * * *